United States Patent [19]
Weaver

[11] Patent Number: 5,667,068
[45] Date of Patent: Sep. 16, 1997

[54] PROTECTIVE COVER FOR AN ENDOSCOPE

[76] Inventor: Stevie W. Weaver, 7514 Yorktown Rd., Louisville, Ky. 40214

[21] Appl. No.: 489,789

[22] Filed: Jun. 13, 1995

[51] Int. Cl.[6] ........................................ A61B 1/00
[52] U.S. Cl. .................. 206/363; 206/438; 600/125; 604/263
[58] Field of Search ........................ 206/363, 438, 206/306, 523, 524, 588, 592; 600/121, 125; 604/259, 264, 263

[56] References Cited

U.S. PATENT DOCUMENTS

| | | | |
|---|---|---|---|
| 3,738,173 | 6/1973 | Sato | 206/438 |
| 4,164,285 | 8/1979 | Dorman | 206/306 |
| 4,646,722 | 3/1987 | Silverstein et al. | 600/104 |
| 4,721,097 | 1/1988 | D'Amelio | 600/121 |
| 4,772,275 | 9/1988 | Erlich | 604/280 |
| 4,878,485 | 11/1989 | Adair | 600/122 |
| 4,886,049 | 12/1989 | Dorras | 600/124 |
| 4,974,580 | 12/1990 | Anapliotis | 600/121 |
| 5,168,863 | 12/1992 | Kurtzer | 600/121 |
| 5,217,001 | 6/1993 | Nakao et al. | 600/123 |
| 5,228,851 | 7/1993 | Borton | 433/116 |
| 5,237,984 | 8/1993 | Williams, III et al. | 600/121 |
| 5,325,846 | 7/1994 | Szabo | 600/121 |
| 5,337,731 | 8/1994 | Takahashi et al. | 600/121 |
| 5,406,939 | 4/1995 | Bala | 600/121 |
| 5,415,157 | 5/1995 | Welcome | 206/592 X |

*Primary Examiner*—Bryon P. Gehman
*Attorney, Agent, or Firm*—Scott R. Cox

[57] ABSTRACT

A protective cover for use in the storage of an endoscope comprising a tubular member containing a passageway running lengthwise through the member from proximal to distal end, a tapered portion for holding the endoscope in place as it is inserted into the passageway, wherein the tapered portion is located at or near the proximal end of the tubular member, and a narrowed portion of the passageway located at or near the distal end of the tubular member.

9 Claims, 2 Drawing Sheets

PROTECTIVE COVER FOR AN ENDOSCOPE

BACKGROUND OF INVENTION

1. Field of Invention

This invention relates to protective devices for medical instruments. In particular, it relates to a protective device for covering the distal end of an endoscope.

2. Prior Art

Endoscopes are medical instruments which enable a relatively non-intrusive visual inspection of and treatment of internal body tissues. One common use for such endoscope is to visually inspect body tissue associated with the digestive track. Typically, an endoscope includes a long flexible tubular member which is inserted into the body and extended to the area of the body to be analyzed. The tubular insertion member of the endoscope generally contains optical fibers for carrying light energy into the patient and for carrying organized visual information out of the patient. The member may also include an elongated lumen for inserting therapeutic instruments into the patient, for example, to biopsy portions of the digestive track.

The operating distal end of the endoscope, which is generally inserted into the body and which is controlled by the endoscopist, is generally quite fragile. This end is usually constructed of lenses of glass-like material which can be easily broken during cleaning of the endoscope, while drying the endoscope after cleaning or while the endoscope is being stored.

Each time an endoscope is used, it must be thoroughly cleaned and disinfected. As a result of the necessity of such disinfection, a number of protective covers have been designed to cover endoscopes. Generally, these protective covers are quite thin and are designed to be attached over the endoscope and remain attached to the endoscope after insertion into the patient during the procedure. For example, U.S. Pat. No. 4,886,049 discloses a thin medical instrument cover, tubular in shape and open at each end, designed to cover an endoscope. A similar sheath made of a thin, flexible material such as rubber is disclosed in U.S. Pat. No. 5,217,001. See also U.S. Pat. Nos. 4,646,722, 5,228,851 and 5,237,984. In addition to sheaths for covering the distal end of an endoscope, there has also been disclosed thin, draping mechanisms for covering medical instruments including, specifically, endoscopes. See, for example, U.S. Pat. Nos. 5,325,846, 4,522,196, 5,337,731 and 5,168,863.

Each of these protective covers for endoscopes must be quite thin and pliable so they can fit over the endoscope with close tolerances and still be inserted into the patient without causing trauma to the patient. While these devices are quite useful to protect the distal end of the endoscope while it is being used within a patient, they are not designed to protect the endoscope after it has been cleaned or when it is in storage.

Thus, there is a need for a device which will cover the fragile, distal end of the endoscope, both while it is drying after being disinfected and while it is in storage.

Accordingly, it is an object of this invention to disclose a protective cover for use in the storage of endoscopes.

It is a further object of this invention to disclose a protective cover for use in the storage of endoscopes which can also be used to check the lighting for the endoscope prior to its use.

It is a still further object of this invention to disclose a protective covering for use in the storage of endoscopes which is both easy to use and inexpensive to produce.

These and other objects can be obtained by the disclosed design for a cover for use in the storage of endoscopes.

SUMMARY OF INVENTION

The instant invention is a protective cover for use in the storage of an endoscope comprising a tubular member containing a passageway running lengthwise through said member from proximal to distal end, a tapered portion of the passageway for holding said endoscope in place as it is inserted into the passageway while still permitting the gradual insertion of said endoscope into the passageway, wherein said holding portion is located at the proximal end of the tubular member, and a narrowed portion of the passageway at the distal end of the tubular member.

DETAILED DESCRIPTION OF THE PREFERRED EMBODIMENT

The device of the instant invention is a protective cover (10) for use in the storage of an endoscope. An endoscope is generally an elongated medical instrument whose distal portion is fragile. Because of the cost of such instruments, they are often reused. However, before they can be reused, they must, of course, be disinfected. After each such disinfection, the instruments are generally placed in a position for drying and storage until their next use. Once an endoscope is needed, it is removed from storage and transported to the room in the medical facility where the endoscope procedure will be performed. During storage and transportation, the fragile distal end of the endoscope must be protected from damage. The device of the instant invention is a protective cover designed for use in the storage and transportation of such endoscopes.

Figure 1:
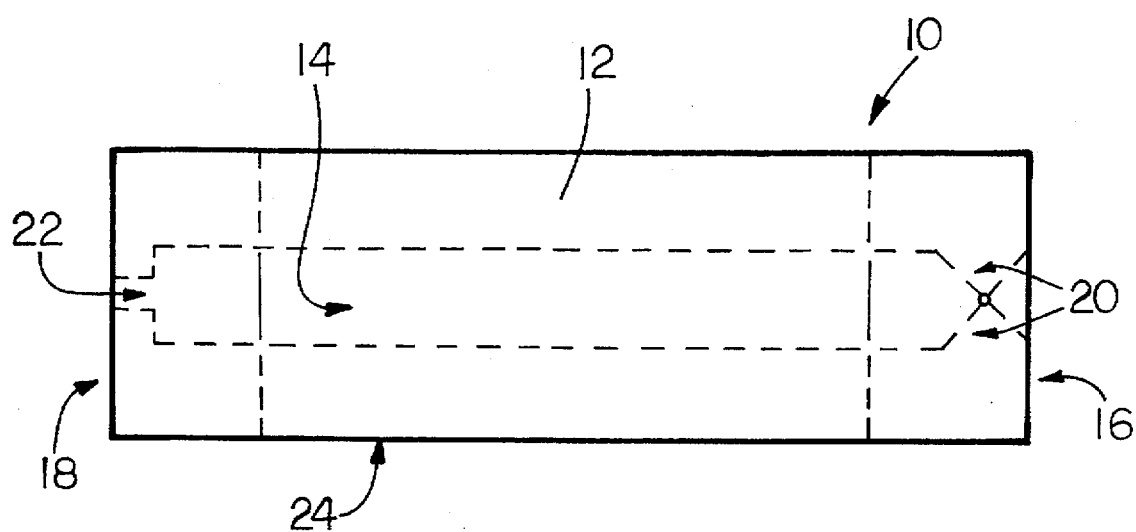
FIG. 1 is a side, cut-away view of the protective cover for use in the storage of an endoscope.

The protective cover (10) of the instant invention is comprised of a tubular member (12) containing a passageway (14) running lengthwise through said member from proximal end (16) to distal end (18). A tapered portion (20) for holding said endoscope in place within the passageway after insertion is located near the proximal end (16) of the protective cover. Near the distal end of the protective cover is preferably a narrowed portion (22) of the passageway (14) and preferably a closing means for closing said narrowed portion (22) to prevent light from entering said passageway (14) from the distal end of the protective cover when said narrowed portion is closed. See FIG. 1.

Figure 3:
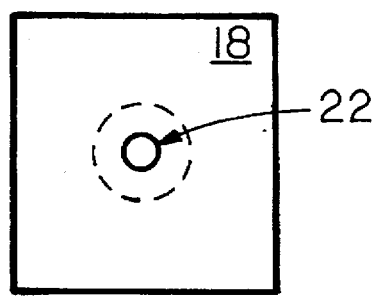
FIG. 3 is a distal end view of the protective cover showing the narrowed portion of the opening in said distal end.
Figure 2:
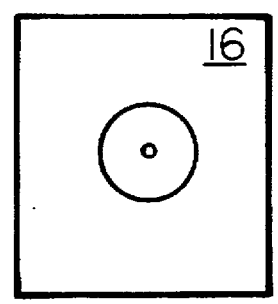
FIG. 2 is an end view of the proximal end of the protective cover.

The protective cover (10) is generally formed from inexpensive elastomeric materials. Suitable elastomeric materials include polymeric resinous materials such as natural and synthetic rubber, thermoplastic polymeric materials such as polyethylene, polyproplene, and polystyrene and other such materials. In a preferred embodiment, the material is a lightweight polystyrene foam. The protective cover (10)

should be of sufficient length to cover the fragile end of the endoscope, preferably from about 10 to about 40 centimeters in length. In addition, the protective cover should be of sufficient thickness so that it can absorb a blow delivered to said cover without damaging the endoscope secured within it. Preferably, the thickness of the protective cover should be at least about 1.0 to about 5.0 centimeters. The shape of the protective cover is not particularly critical, although it should contain at least one flat side so that the cover will not roll. In a preferred embodiment, the cross section of the protective cover is square. See FIGS. 2 and 3.

The diameter of the passageway contained within the protective cover is dependent upon the diameter of the endoscope being used. Notwithstanding, this passageway should be of sufficient diameter to easily receive an endoscope within said passageway. The passageway should be at least 0.1 cm. greater in diameter than the overall diameter of the portion of the endoscope that is to be covered.

The proximal end (16) of the protective cover preferably contains a tapered restriction means to restrict, but not stop, the introduction of the endoscope into the passageway. Preferably, this restriction means is a tapered portion (20) of the passageway (14). The diameter of the passageway is approximately the same as, or preferably smaller than, the diameter of the endoscope. In a preferred embodiment the distance between the sides of the passageway narrows to as small as about 1 mm at the tapered portion (20). Because the preferred material for the construction of the protective cover is a polystyrene foam, the endoscope can be inserted and fit through this tapered portion (20) near the proximal end (16) of the tubular member. Once the endoscope has been inserted into the protective cover, this tapered portion of the passageway tends to retain the protective cover (10) on the endoscope.

To further assist in holding the protective cover onto the endoscope a closing means such as elastic tightener (not shown) may be used to encircle the outside surface (24) of the protective cover of the tubular member (12) which contains the tapered portion (20) of the protective cover. By tightening the elastic tightener around the tapered portion (20) of the passageway, further pressure will be placed on the outside of the endoscope, thus holding it securely in place.

While a single tapered portion (20) of the passageway for holding the endoscope is preferred, two or more such tapered portions may be utilized to provide further support for the endoscope. In addition, tapered portions of greater and lesser diameter may be contained within the tubular member (12). By placing elastic tighteners around these various sections and by tightening said elastic tighteners, endoscopes, the distal end of which has different diameters, may be held securely by the protective cover (10).

Figure 4:
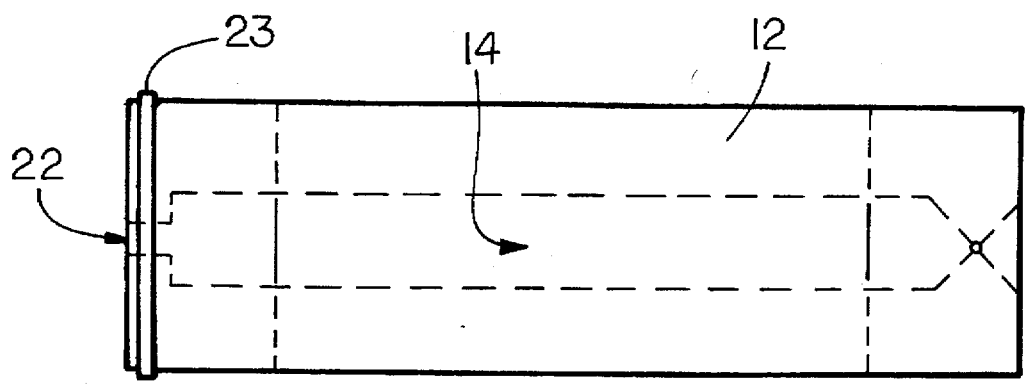
FIG. 4 is a side, cutaway view of the protective cover showing the first embodiment of the device to close the distal end of the protective cover.

The remaining length of the passageway (14) to the narrowed opening at the distal end should be approximately the same diameter. Within about 0.5 to about 4.0 cm. from the distal end (18) of the tubular member (12), the passageway (14) narrows to a narrowed portion (22) extending to the distal end of the tubular member. This narrowed portion (22) may be as small as about 0.1 cm., but preferably should be no less than about 0.2 cm. The opening should be of sufficient size for air to enter through the narrowed opening and pass through the passageway (14). A means may be secured to the distal end of the protective cover to close this narrowed portion (22). Any conventional means for closing a passageway may be utilized. In one preferred embodiment, an elastic member (not shown) surrounds the distal end (18) of the tubular member 23, preferably within a trough formed in the outside surface (24) of the tubular member (12). As this elastic is drawn tighter, the narrowed portion (22) closes. See FIG. 4. Alternatively, the distal end of the tubular member can be constricted by the technician simply by squeezing the distal end until the narrowed portion of the passageway is closed.

Figure 5:
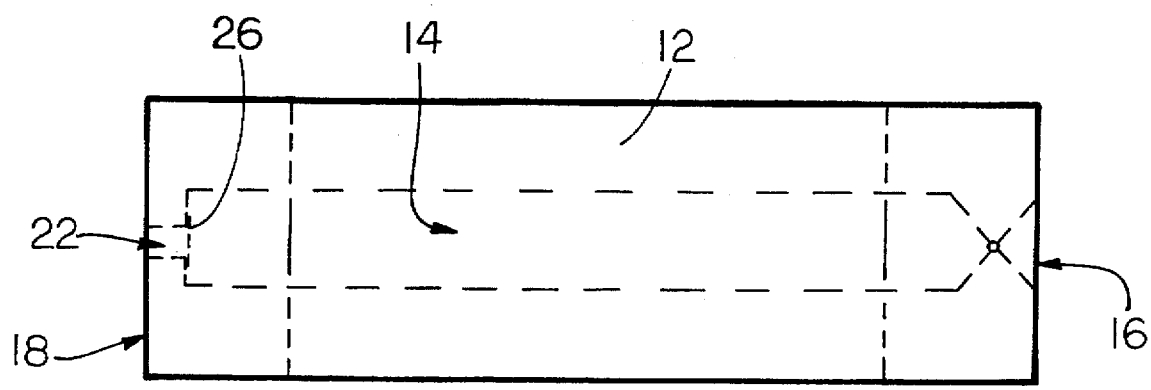
FIG. 5 is a side, cutaway view of the protective cover showing the second embodiment side to close the distal end of the protective cover.

In an alternative preferred embodiment a closing device such as a flap (26), is secured within the passageway at approximately the location where the narrowed portion (22) of the passageway begins. See FIG. 5. This closing device when it is open permits air to flow into the passageway (14). However, when the endoscope is inserted into the tubular member and presses against this closing device or flap, it closes the passageway (14), thus preventing light from entering the passageway.

Closing of the passageway is especially important as one of the preparatory procedures run on the endoscope prior to its usage is a test for white light. This can only be done with the endoscope in a darkened environment. By closing the passageway to prevent light from entering the passageway, this procedure for testing the light of the endoscope can be accomplished.

As is apparent from the foregoing specifications, the present invention is capable of being embodied with various alterations and modifications from those described above. For this reason, it is to be fully understood that all of the foregoing is intended to be merely illustrative and is not intended to limit in any manner the scope of the invention as set forth in the following claims.

I claim:

1. A protective cover for use in the storage of an endoscope comprising
   (a) a tubular member with proximal and distal ends, containing a passageway running lengthwise through said member from said proximal to said distal end,
   (b) a tapered holding means for holding said endoscope in place as it is inserted into the passageway,
   (c) a narrowed portion of the passageway in said tubular member located near its distal end and
   (d) a closing means for closing said distal end of the tubular member so as to prevent light from entering the passageway through the distal end when said closing means closes said distal end, wherein the closing means is a flap which prevents light from entering the passageway through the distal end.

2. The protective cover of claim 1 wherein the tapered holding means is a tapered portion extending inwardly into said passageway near the proximal end of the protective cover.

3. The protective cover of claim 1 wherein an elastic tightener surrounds said tubular member near its distal end.

4. The protective cover of claim 1 wherein the tapered holding means is a tapered portion extending inwardly into said passageway near the proximal end of the protective cover.

5. The protective cover of claim 4 wherein more than one tapered portion are contained within the passageway of the tubular member.

6. The protective cover of claim 1 wherein the tubular member is square in cross-section.

7. The protective cover of claim 1 wherein the tubular member is from about 10 to about 40 centimeters in length.

8. The protective cover of claim 1 wherein the thickness of the tubular member is from about 1.0 to about 5.0 cm.

9. The protective cover of claim 1 wherein the protective flap is secured within the passageway in said tubular member.

* * * * *